US010052433B2

(12) United States Patent
Rajadhyax et al.

(10) Patent No.: US 10,052,433 B2
(45) Date of Patent: Aug. 21, 2018

(54) INTRAVENOUS FLUID MONITORING SYSTEM (71) Applicants: Devesh Rajadhyax, Navi Mumbai (IN); Manish Raghunathan Nair, Kalyan (IN); Shruti Shashi Kumar, Mumbai (IN); Tushar Ratanghayra, Dombivli (IN); Rajashree Rajadhyax, Navi Mumbai (IN); Siddhesh Wagle, Mumbai (IN)

(72) Inventors: Devesh Rajadhyax, Navi Mumbai (IN); Manish Raghunathan Nair, Kalyan (IN); Shruti Shashi Kumar, Mumbai (IN); Tushar Ratanghayra, Dombivli (IN); Rajashree Rajadhyax, Navi Mumbai (IN); Siddhesh Wagle, Mumbai (IN)

( * ) Notice: Subject to any disclaimer, the term of this patent is extended or adjusted under 35 U.S.C. 154(b) by 0 days.

(21) Appl. No.: 15/361,091

(22) Filed: Nov. 25, 2016

(65) Prior Publication Data
US 2018/0099083 A1 Apr. 12, 2018

(51) Int. Cl.
A61M 5/14 (2006.01)
G06F 19/00 (2018.01)
G16H 40/63 (2018.01)

(52) U.S. Cl.
CPC .......... *A61M 5/14* (2013.01); *G06F 19/3406* (2013.01); *G06F 19/3468* (2013.01); *G16H 40/63* (2018.01); *A61M 2205/3393* (2013.01); *A61M 2205/3546* (2013.01); *A61M 2205/3576* (2013.01); *A61M 2205/502* (2013.01); *A61M 2205/52* (2013.01); *A61M 2205/6009* (2013.01)

(58) Field of Classification Search
CPC .. G06F 19/3406; G06F 19/3468; G06F 19/30; G06F 19/32; G06F 19/321; G06F 19/325; G06F 19/326; G06F 19/34; G06F 19/3418; G06F 19/3462; A61M 5/14; A61M 2205/33; A61M 2205/3331; A61M 2205/3334; A61M 2205/3379; A61M 2205/3389; A61M 2205/3393; A61M 2205/3523; A61M 2205/3546; A61M 2205/3561; A61M 2205/3576; A61M 2205/60; A61M 2205/6009; A61M 2205/502; A61M 2205/52; G16H 20/00; G16H 20/17; G16H 40/63
USPC ........... 340/511, 539.12, 603, 606, 612, 613, 340/870.01
See application file for complete search history.

(56) References Cited

U.S. PATENT DOCUMENTS

2014/0135732 A1* 5/2014 Spronken .......... A61M 5/16895
604/500

* cited by examiner

Primary Examiner — Brian Wilson (57) ABSTRACT

An intravenous (IV) fluid monitoring system includes a sensing element, a user locator device, a location server, and an analytics server. The sensing element senses weight of an IV bag and transmits weight data and a first ID signal corresponding to the IV bag. The user locator device transmits a second ID signal corresponding to a user. The location server stores and periodically updates sets of ID data and locations of a set of users and a plurality of IV bags. The analytics server stores and periodically updates a set of weight data of the plurality of IV bags. The analytics server implements a machine learning algorithm to determine a threshold weight and a threshold rate of flow of the IV fluid in the IV bag and transmits a notification signal to a user who is nearest to the IV bag that needs attention.

20 Claims, 5 Drawing Sheets

INTRAVENOUS FLUID MONITORING SYSTEM

BACKGROUND

Field of the Invention

The present invention relates generally to systems for monitoring intravenous (IV) fluids in IV bags and more particularly, to a system for real-time monitoring of IV fluid in an IV bag.

Description of the Related Art

Typically, IV therapy includes administration of IV fluids directly into the bloodstream of a patient. The examples of the IV fluids include medicines, glucose, saline, blood, blood plasma, and the like. The most common and economical way of implementing the IV therapy is using gravity-fed IV infusion systems that include an IV bag, an IV flow line, and, a needle inserted into a vein of the patient. The IV bag, which is suspended from a stand at a height greater than the height at which the patient is resting, stores the IV fluid. The IV fluid flows into the IV flow line and into the needle due to gravitational force and is administered into the patient's vein. A nurse or a health care professional monitors a level of the IV fluid in the IV bag. The nurse identifies a threshold level of the IV fluid in the IV bag such that a decrease in the level of the IV fluid below the threshold level impedes the administration of the IV fluid into the patient's vein. When the level of the IV fluid in the IV bag reaches the threshold level, the nurse replaces the IV bag with a new IV bag before the IV fluid completely drains out from the IV bag. The replacement of the IV bag based on the determination of the threshold level ensures that the IV fluid is administered without any interruption in the continuous administration of the IV fluid to the patient. Due to factors such as negligence, lack of skill in identifying the threshold level, catering to responsibilities other than monitoring the IV fluid, and the like, the nurse may fail to replace the IV bag in time. The failure to replace the IV bag in time results in an interruption in the continuous administration of the IV fluid to the patient, which is detrimental to the health of the patient.

A known technique to prevent the aforementioned problem is to use an IV fluid monitoring system that includes a level sensor to generate a sensor signal, which is indicative of the level of the IV fluid in the IV bag. The IV fluid monitoring system further includes a processor that is configured to compare the sensor signal with the threshold level corresponding to the IV fluid in the IV bag. When the level of the IV fluid reaches the threshold level, the processor generates a notification signal in form of an alarm or a message, which is wirelessly transmitted to a hand-held device carried by the nurse. The nurse replaces the IV bag in response to the notification signal. However, disturbances in the surroundings, such as an accidental push to the stand, incorrect placement of the IV bag on the stand, and the like will change the position of the IV bag, which in turn results in aberrations in the level of the IV fluid in the IV bag that is being sensed by the level sensor. Consequently, the sensor signal indicates an incorrect measure of the level of the IV fluid remaining in the IV bag. Thus, the processor generates the notification signal in response to the incorrect measure of the level of the IV fluid in the IV bag. The incorrect notification signal results in an interruption in the administration of the IV fluid.

A known technique to prevent the aforementioned problem is to include a weight sensor, instead of the level sensor, in the IV fluid monitoring system to generate the sensor signal, which is indicative of weight of the IV fluid in the IV bag. The processor is configured to compare the sensor signal with threshold weight corresponding to the IV fluid in the IV bag. The threshold weight of the IV fluid in the IV bag is defined such that decrease in the weight of the IV fluid below the threshold weight impedes the administration of the IV fluid. When the weight sensor detects the threshold weight of the IV fluid in the IV bag, the processor generates the notification signal. The IV fluid monitoring system with the weight sensor accurately generates the notification signal irrespective of the position of the IV bag, in contrast to the IV fluid monitoring system with the level sensor. However, for the IV fluid monitoring system with either the level or the weight sensor, modification in size and material of the IV bag requires modification in the threshold level or the threshold weight for the corresponding IV bag. The nurse has to reconfigure the corresponding processor to compare the sensor signal with the modified threshold level or the modified threshold weight of the IV fluid. The nurse may fail to reconfigure the processor due to reasons such as emergency attention required by critically ill patients leading to negligence, monitoring multiple patients, lack of know-how corresponding to process of reconfiguration of the processor, and the like. Hence, the processor generates the notification signal in response to an incorrect threshold level or an incorrect threshold weight of the IV fluid in the IV bag, which is undesirable.

After the IV fluid monitoring system generates the notification signal and raises the alarm, the nurse reaches the patient and replaces the IV bag with a new IV bag. The time required for the nurse to reach and change the IV bag depends on the location of the nurse with respect to the IV bag. If the nurse is located far away and hence, reaches the patient after the IV bag becomes empty, the administration of the IV fluid to the patient is interrupted.

SUMMARY

An object of the present invention is to have an IV fluid monitoring system for monitoring the IV fluid in the IV bag to accurately determine the threshold weight of the IV fluid in the IV bag.

Another object of the present invention is to prevent the interruption in the administration of the IV fluid to the patient.

In an embodiment of the present invention, an intravenous (IV) fluid monitoring system is provided. The IV fluid monitoring system assists a set of users, including a user, to monitor and manage multiple IV bags, including an IV bag. Each IV bag of the multiple IV bags stores IV fluid. The IV fluid monitoring system includes a sensing element, a user locator device, a location server, and an analytics server. The sensing element is attached to the IV bag and outputs weight data and a first identification (ID) signal, which includes a first ID number of the IV bag. The user locator device outputs a second ID signal, which includes a second ID number of the user. The location server receives first and second ID data. The first ID data includes the first ID number and a corresponding first location of the IV bag. Similarly, the second ID data includes the second ID number and a second location of the user. The location server stores a first set of ID data, which includes sets of ID numbers and locations of the multiple IV bags, and a second set of ID data, which includes sets of ID numbers and locations of the set of users. The location server updates the first and second sets of ID data with the first and second ID data, respectively, and outputs updated first and second sets of ID data. The analytics server stores a set of weight data and updates the set of weight data with the weight data received from the sensing element. The analytics server further receives the updated first and second sets of ID data, and determines at least one ID number of at least one corresponding user based on a proximity of a location of each user of the set of users to the location of the IV bag. The analytics server uses a machine learning algorithm configured to determine a threshold rate of flow of the IV fluid and a threshold weight of the IV fluid in the IV bag based on the updated set of weight data, the updated first and second sets of ID data, and a location of the at least one corresponding user. Further, the analytics server generates at least one notification signal that includes the first ID data, and the at least one ID number, and at least one of the threshold weight and the threshold rate of flow.

In another embodiment of the present invention, a method for monitoring IV fluid is provided. The method assists a set of users to monitor and manage multiple IV bags, each of which includes the IV fluid. The multiple IV bags include an IV bag and the set of users includes a user. Weight data and a first ID signal, which includes a first ID number of the IV bag, are output by a sensing element that is attached to the IV bag. A second ID signal, which includes a second ID number of the user, is output by a user locator device. First ID data, which includes the first ID number and a corresponding first location of the IV bag, is received by a location server. Similarly, second ID data, which includes the second ID number and a corresponding second location of the user, is received by the location server. First and second sets of ID data are stored in the location server, the first and second sets of ID data are updated with the first and second ID data, respectively, and updated first and second sets of ID data are generated. The first set of ID data includes sets of ID numbers and corresponding locations of the multiple IV bags. Similarly, the second set of ID data includes sets of ID numbers and corresponding locations of the set of users. Further, a set of weight data is stored in an analytics server, the set of weight data is updated with the weight data, and an updated set of weight data is generated. The set of weight data corresponds to the multiple IV bags. Further, at least one ID number of at least one corresponding user is determined based on a proximity of a location of each of the set of users to the location of the IV bag. A machine learning algorithm is configured to determine a threshold rate of flow of the IV fluid and a threshold weight of the IV fluid in the IV bag based on the updated set of weight data, the updated first and second sets of ID data, and a location of the at least one corresponding user. Furthermore, at least one notification signal that includes the first ID data, and the at least one ID number, and at least one of the threshold weight and the threshold rate of flow is generated.

Various embodiments of the present invention provide an IV fluid monitoring system for assisting a set of users to monitoring and manage IV fluids in multiple IV bags. Examples of the set of users are health care professionals such as nurses, doctors, and the like. The IV fluid monitoring system includes a sensing element, a user locator device, a location server, and an analytics server. The sensing element senses the weight of an IV bag and transmits the weight data and a first ID signal, which includes a first ID number of the IV bag. The user locator device transmits a second ID signal, which includes a second ID number of the user. The location server stores and periodically updates first and second sets of ID data. The first set of ID data includes sets of ID numbers and corresponding locations of multiple IV bags. Similarly, the second set of ID data includes sets of ID numbers and corresponding locations of the set of users. The analytics server stores and periodically updates a set of weight data of multiple IV bags. The analytics server determines a user nearest to the IV bag based on the locations of the set of users and the location of the IV bag. The analytics server implements a machine learning algorithm to determine a threshold level and a threshold rate of flow of the IV fluid in the IV bag based on the location of the nearest user, the updated set of weight data, and the updated set of ID data of both multiple IV bags and the set of users. The analytics server generates a notification signal which includes the threshold level and the rate of flow of the IV fluid in the IV bag, and the ID data of the IV bag and the nearest user. The notification signal is displayed by a user notification device of the user who is nearest to the IV bag that needs attention.

Thus, the IV fluid monitoring system ensures an uninterrupted administration of the IV fluids to patients irrespective of the location of the users. Further, the IV fluid monitoring system detects anomalies in the rate of flow of the IV fluid and avoids irregularities in the administration of the IV fluids to the patients.

BRIEF DESCRIPTION OF DRAWINGS

The present invention, together with objects and advantages thereof, may best be understood by reference to the following description of embodiments thereof shown in the accompanying drawings. Elements in the drawings are illustrated for simplicity and clarity and have not necessarily been drawn to scale.

DETAILED DESCRIPTION OF THE EMBODIMENTS

The detailed description of the appended drawings is intended as a description of the currently preferred embodiments of the present invention, and is not intended to represent the only form in which the present invention may be practiced. It is to be understood that the same or equivalent functions may be accomplished by different embodiments that are intended to be encompassed within the spirit and scope of the present invention.

Health care institutions such as hospitals and nursing homes employ one or more health care professionals (also referred to as users) to provide diagnosis and treatment to one or more patients. Examples of the users include physicians, doctors, nurses, and the like. The health care institutions usually have an IV fluid infusion system for each of its one or more patients. The most economical and hence, commonly preferred method of IV fluid infusion is a gravity-fed IV infusion. The gravity-fed IV fluid infusion system includes an IV bag, an IV flow line, and a needle. The IV bag is suspended on a stand placed near a bed of each of the one or more patients. The IV bag is connected to the IV flow line, which is further connected to the needle that is inserted into a vein of the patient. Continuous administration of the IV fluid by the IV fluid infusion system is ensured by implementing an IV fluid monitoring system connected to the gravity-fed IV fluid infusion system.

Figure 1:
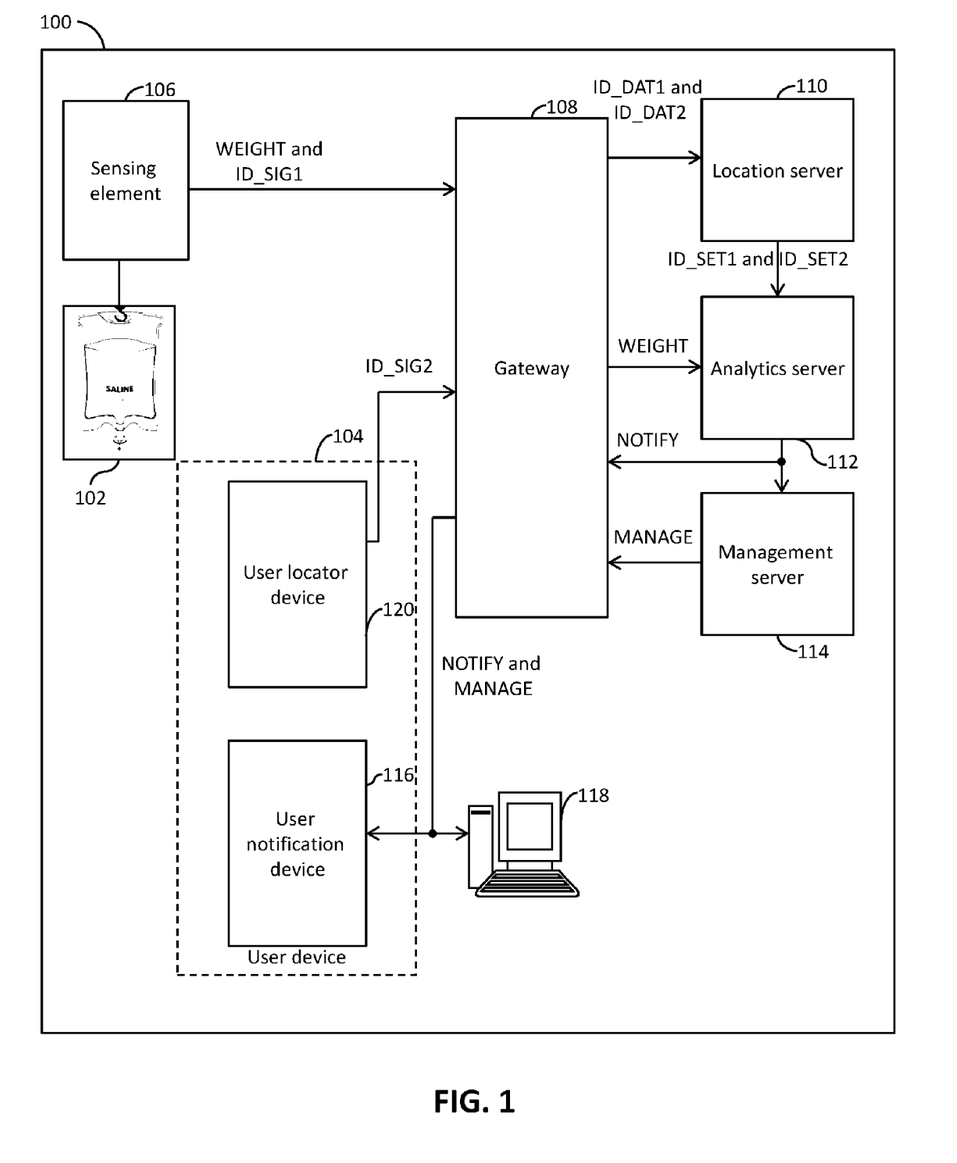
FIG. 1 is a schematic block diagram of an intravenous (IV) fluid monitoring system in accordance with an embodiment of the present invention.

Referring now to FIG. 1, a schematic block diagram of an IV fluid monitoring system 100 in accordance with an embodiment of the present invention is shown. The IV fluid monitoring system 100 assists a set of users in monitoring multiple IV bags including an IV bag 102 in the health care institutions. Each user of the set of users is a nurse or a health care professional who is in charge of catering to the needs of the one or more patients.

The IV fluid monitoring system 100 includes a set of user devices 104 (one of which is shown) carried by the corresponding set of users, multiple sensing elements 106 (one of which is shown), a gateway 108, a location server 110, an analytics server 112, and a management server 114. The IV fluid monitoring system 100 further includes a set of user notification devices including first and second user notification devices 116 and 118. Each user device 104 includes a corresponding user locator device 120 and the corresponding first user notification device 116. Examples of the first user notification device 116 include hand-held devices, such as mobile phones, tablets, phablets, personal digital assistants (PDAs), and the like. Examples of the second user notification device 118 include desktops, laptops, and the like. In the presently preferred embodiment, the first user notification device 116 is carried by a user of the set of users. The user may attach the user locator device 120 to his or her uniform. Further, the second user notification device 118 is accessible and visible to the entire set of users.

The sensing element 106 is connected to the IV bag 102 and generates weight data (hereinafter referred to as "WEIGHT") of the IV bag 102. The sensing element 106 generates a first identification (ID) signal (hereinafter referred to as "ID_SIG1"), which includes a first ID number (hereinafter referred to as "ID_NUM1"). The ID_NUM1 corresponds to the IV bag 102, which is connected to the sensing element 106. When the IV bag 102 is replaced with a new IV bag, the ID_SIG1 corresponds to the new IV bag. The sensing element 106 transmits the ID_SIG1 and WEIGHT to the gateway 108.

The user locator device 120 generates and transmits a second ID signal (hereinafter referred to as "ID_SIG2") to the gateway 108. The ID_SIG2 includes a second ID number (hereinafter referred to as "ID_NUM2") corresponding to a user. In the presently preferred embodiment, each sensing element of the multiple sensing elements and each user locator device of the set of user locator devices are structurally and functionally similar to the sensing element 106 and the user locator device 120, respectively, which will be explained in detail in conjunction with FIG. 2 below.

The gateway 108 receives the ID_SIG1, ID_SIG2, and WEIGHT. In an embodiment, the gateway 108 includes a gateway receiver (not shown) and a gateway controller (not shown). The gateway receiver receives the ID_SIG1 and ID_SIG2 as first and second radio signals, respectively, using a wireless protocol. Examples of the wireless protocols include wireless-fidelity (Wi-Fi), Bluetooth, ZigBee, and the like. The gateway controller determines a received signal strength indicator (RSSI) corresponding to each of the ID_SIG1 and ID_SIG2. It is well known to a person skilled in the art that a received signal strength indicator (RSSI) of a radio signal is a measurement of power in a radio signal that is received at the gateway receiver. Further, the RSSI of the radio signal is indicative of a distance of a source of the radio signal from the gateway receiver. In the presently preferred embodiment, the sources of the ID_SIG1 and ID_SIG2 are the sensing element 106 and the user locator device 120, respectively. The gateway controller determines first and second locations corresponding to the sensing element 106 and the user locator device 120, respectively. Since the sensing element 106 is attached to the IV bag 102, the first location also indicates a location of the IV bag 102. Similarly, since the user locator device 120 is carried by the user, the second location also indicates a location of the user. Thus, the gateway controller determines the locations of the IV bag 102 and the user based on the RSSI of the ID_SIG1 and ID_SIG2, respectively.

Further, the gateway controller retrieves the ID_NUM1 and ID_NUM2 from the ID_SIG1 and ID_SIG2, respectively. The ID_NUM1 and the first location are collectively referred to as first ID data (hereinafter referred to as "ID_DAT1"). Similarly, the ID_NUM2 and the second location are collectively referred to as second ID data (hereinafter referred to as "ID_DAT2"). The gateway 108 transmits the ID_DAT1 and ID_DAT2 of the IV bag 102 and the user, respectively, to the location server 110. Furthermore, the gateway 108 transmits the WEIGHT to the analytics server 112.

The location server 110 receives and stores first and second sets of ID data (not shown) corresponding to the multiple IV bags and the set of users, respectively. The first set of ID data includes ID numbers and the locations of the multiple IV bags. Similarly, the second set of ID data includes ID numbers and the locations of the set of users. The location server 110 periodically receives and updates the locations of the multiple IV bags in the first set of ID data based on the first clock signal. Similarly, the location server 110 periodically receives and updates locations of the set of users in the second set of ID data based on the second clock signal. Thus, the location server 110 generates updated first and second sets of ID data. For example, the location server 110 wirelessly receives the ID_DAT1 and ID_DAT2, updates the first and second sets of ID data, and generates updated first and second sets of ID data (the updated first and second sets of ID data are hereinafter referred to as "ID_SET1" and "ID_SET2", respectively).

The analytics server 112 receives and stores a set of weight data corresponding to the multiple IV bags in each clock cycle of the first clock signal. The analytics server 112 also receives the ID_SET1 and ID_SET2. In the presently preferred embodiment, the analytics server 112 includes a processor (not shown) and a memory (not shown). The processor compares a location of each of the multiple IV bags with the locations of the set of users. Thus, the processor determines at least one user of the set of users for each IV bag, such that the at least one user is nearest to the corresponding IV bag of the multiple IV bags. In an embodiment, the processor determines one user, who is nearest to the IV bag 102. In another embodiment, the processor determines two users of the set of users for the IV bag 102, such that a distance of each of the two users from the IV bag 102 is less than a distance of each of the remaining users of the set of users from the IV bag 102. Thus, if a first user of the two users is unable to respond because of responsibilities other than monitoring the IV fluid, a second user of the two users responds and monitors the IV fluid in the IV bag 102.

In the presently preferred embodiment, the processor further implements a machine learning algorithm that is configured to generate a threshold rate of flow of the IV fluid and a threshold weight of the IV fluid in each IV bag of the multiple IV bags based on the set of weight data, ID_SET1, and ID_SET2. The machine learning algorithm estimates a period of time that is required by a nearest user to reach the location of the IV bag 102 and replace it with a new IV bag. The machine learning algorithm also estimates a rate of flow of the IV fluid in the IV bag 102. Further, the machine learning algorithm determines the threshold weight of the IV fluid in the IV bag 102 based on the estimated period of time and the estimated rate of flow of the IV fluid. The threshold weight of the IV fluid in the IV bag 102 is defined such that a decrease in weight of the IV fluid below the threshold weight impedes the administration of the IV fluid to the patient.

In another embodiment, the machine learning algorithm determines first and second threshold weights of the IV fluid. The first threshold weight of the IV fluid in the IV bag 102 indicates that the weight of the IV fluid in the IV bag 102 will reach the second threshold weight in a predetermined interval of time. The second threshold weight of the IV fluid in the IV bag 102 is similar to the threshold weight and a decrease in the weight of the IV fluid below the second threshold weight impedes the administration of the IV fluid. Thus, the first threshold weight warns the user that the IV bag 102 will need replacement after the predetermined interval of time. For example, if the predetermined interval of time is 5 minutes, the weight of the IV fluid in the IV bag 102 will reach the second threshold weight after 5 minutes of reaching the first threshold weight.

Further, the machine learning algorithm also determines the threshold rate of flow to indicate that the threshold rate of flow of the IV fluid draining out of the IV bag 102 is not within a range of the rate of flow of the IV fluid that is prescribed by the health care professional. The updated set of the weight data, ID_SET1, and ID_SET2 train the machine learning algorithm to determine the threshold weight and threshold rate of flow of the IV fluid for each IV bag 102 of the multiple IV bags according to the corresponding nearest user. Machine learning algorithms such as K-means clustering, Naïve Bayes algorithm, Linear regression, and the like are well known in the art.

When at least one of the weight and the rate of flow of the IV fluid in the IV bag 102 is equal to the corresponding threshold weight and the corresponding threshold rate of flow, respectively, the analytics server 112 generates a notification signal (hereinafter referred to as "NOTIFY"). The NOTIFY includes the ID_DAT1, the threshold weight, the threshold rate of flow of the IV fluid of the corresponding IV bag 102, and the ID number of the corresponding nearest user. In an embodiment, the analytics server 112 generates the NOTIFY based on a first clock signal (not shown).

The management server 114 receives the NOTIFY and generates a management signal (hereinafter referred to as "MANAGE"). In one embodiment, the management server 114 stores management data, which includes information corresponding to the stock of the available IV bags and estimates a period of time after which the stock of IV bags would be replenished. In another embodiment, the management server 114 further stores information of the notification signals corresponding to each user. Thus, the management server 114 maintains a record of delays in response of each user after the user receives the NOTIFY. The MANAGE includes a reminder, a user report, and the like. The gateway 108 receives the NOTIFY and MANAGE and forwards them to the first and second user notification devices 116 and 118.

The first user notification device 116 displays the NOTIFY when the ID_NUM1 matches the ID number of the nearest user from the NOTIFY. The second user notification device 118 displays the NOTIFY and MANAGE. The structure and function of the first and second user notification devices 116 and 118 will be explained in detail in conjunction with FIG. 2 below.

Figure 2:
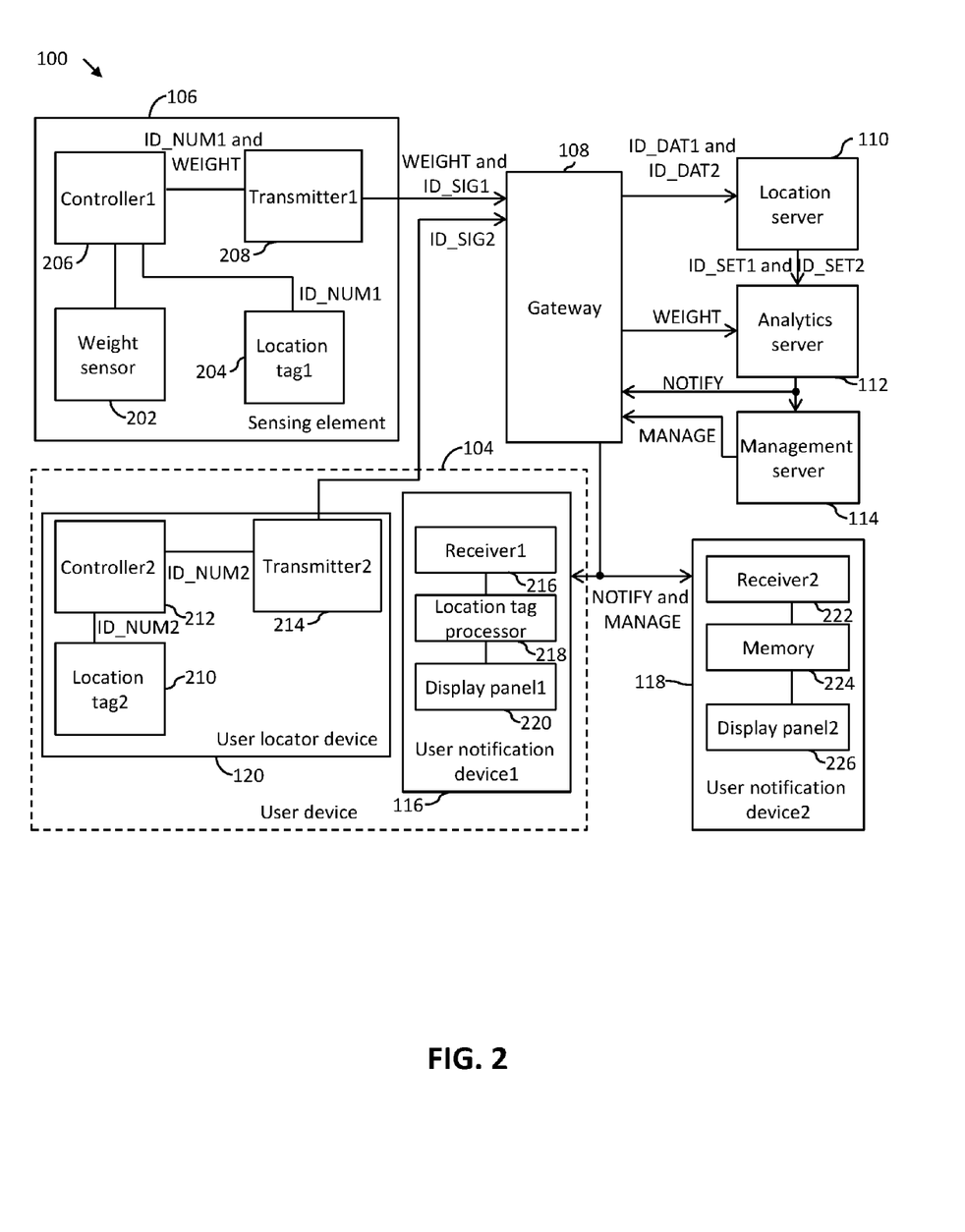
FIG. 2 is a schematic block diagram of a sensing element, a user locator device, and first and second user notification devices of the IV fluid monitoring system of FIG. 1 in accordance with an embodiment of the present invention.

Referring now to FIG. 2, a schematic block diagram of the sensing element 106, the user locator device 120, and the first and second user notification devices 116 and 118 of the IV fluid monitoring system 100 of the FIG. 1 in accordance with an embodiment of the present invention is shown. The sensing element 106 includes a weight sensor 202, a first location tag 204, a first controller 206, and a first transmitter 208. The user locator device 120 includes a second location tag 210, a second controller 212, and a second transmitter 214. The first user notification device 116 includes a first receiver 216, a location tag processor 218, and a first display panel 220. The second user notification device 118 includes a second receiver 222, a memory 224, and second display panel 226. Various examples of the first and second display panels 220 and 226 include seven-segment display, a liquid crystal display (LCD), a light emitting diode (LED) display, and the like.

The weight sensor 202 is coupled with the IV bag 102 and senses the weight of the IV bag 102. The weight sensor 202 generates a weight signal, such that the voltage level of the weight signal is proportional to the weight of the IV bag 102. In one embodiment, the weight sensor 202 includes a load cell. The load cell generates a voltage level of a voltage signal that is in proportion to a force applied on the load cell. Examples of load cells include a resistive load cell and a capacitive load cell.

The first location tag 204 stores ID_NUM1. The first location tag 204 may also store and transmit the type of the IV fluid in the IV bag 102 and the dimensions of the IV bag 102. Various types of the IV fluids include saline, medicines, blood plasma, and the like. In one embodiment, the first location tag 204 is a radio frequency ID (RFID) tag. In another embodiment, the first location tag 204 is a Wi-Fi tag. The second location tag 210 is structurally and functionally similar to the first location tag 204, and stores the ID_NUM2.

The first controller 206 is connected to the first location tag 204 and the weight sensor 202. The first controller 206 receives the weight signal and the ID_NUM1 and generates the WEIGHT and the ID_SIG1. In an embodiment, WEIGHT is a binary number and the value of WEIGHT is proportional to the voltage level of the weight signal. Further, the ID_SIG1 is a radio signal. The first controller 206 transmits the WEIGHT and ID_SIG1 by way of the first transmitter 208 to the gateway 108. Similarly, the second controller 212 is connected to the second location tag 210 and receives the ID_NUM2. The second controller 212 generates and transmits the ID_SIG2 by way of the second transmitter 214 to the gateway 108.

In one embodiment, the first controller 206 operates based on a second clock signal (not shown) and transmits the WEIGHT and ID_SIG1 at periodic intervals of time based on the second clock signal. The second controller 212 operates on a third clock signal and transmits the ID_SIG2 at periodic intervals of time based on the third clock signal. The frequency of the second clock signal may or may not be equal to the frequency of the third clock signal. In another embodiment, the first controller 206 transmits the ID_SIG1 and WEIGHT continuously, and the second controller 212 transmits the ID_SIG2 continuously. The first and second transmitters 208 and 214 wirelessly transmit the WEIGHT, ID_SIG1, and ID_SIG2. The first and second transmitters 208 and 214 support various wireless protocols such as ZigBee, Wi-Fi, Bluetooth, and the like.

The first receiver 216 receives the NOTIFY. The location tag processor 218 stores the ID_NUM2. The location tag processor 218 is connected to the first receiver 216 and receives the NOTIFY that includes ID number of the nearest user to the IV bag 102 having the threshold weight of the IV fluid. The location tag processor 218 compares the ID_NUM2 with the ID number of the nearest user. When the ID_NUM2 matches the ID number of the nearest user, the location tag processor 218 displays the NOTIFY on the first display panel 220. When the ID_NUM2 does not match the ID number of the nearest user, the NOTIFY is not displayed on the first display panel 220.

In one embodiment, the second receiver 222 receives the NOTIFY and MANAGE. The memory 224 is connected to the second receiver 222 and stores a reminder and a report from the MANAGE. The second display panel 226 displays the NOTIFY and MANAGE. The second user notification device 118 is common to the entire set of users, i.e., the hospital staff.

Figure 3:
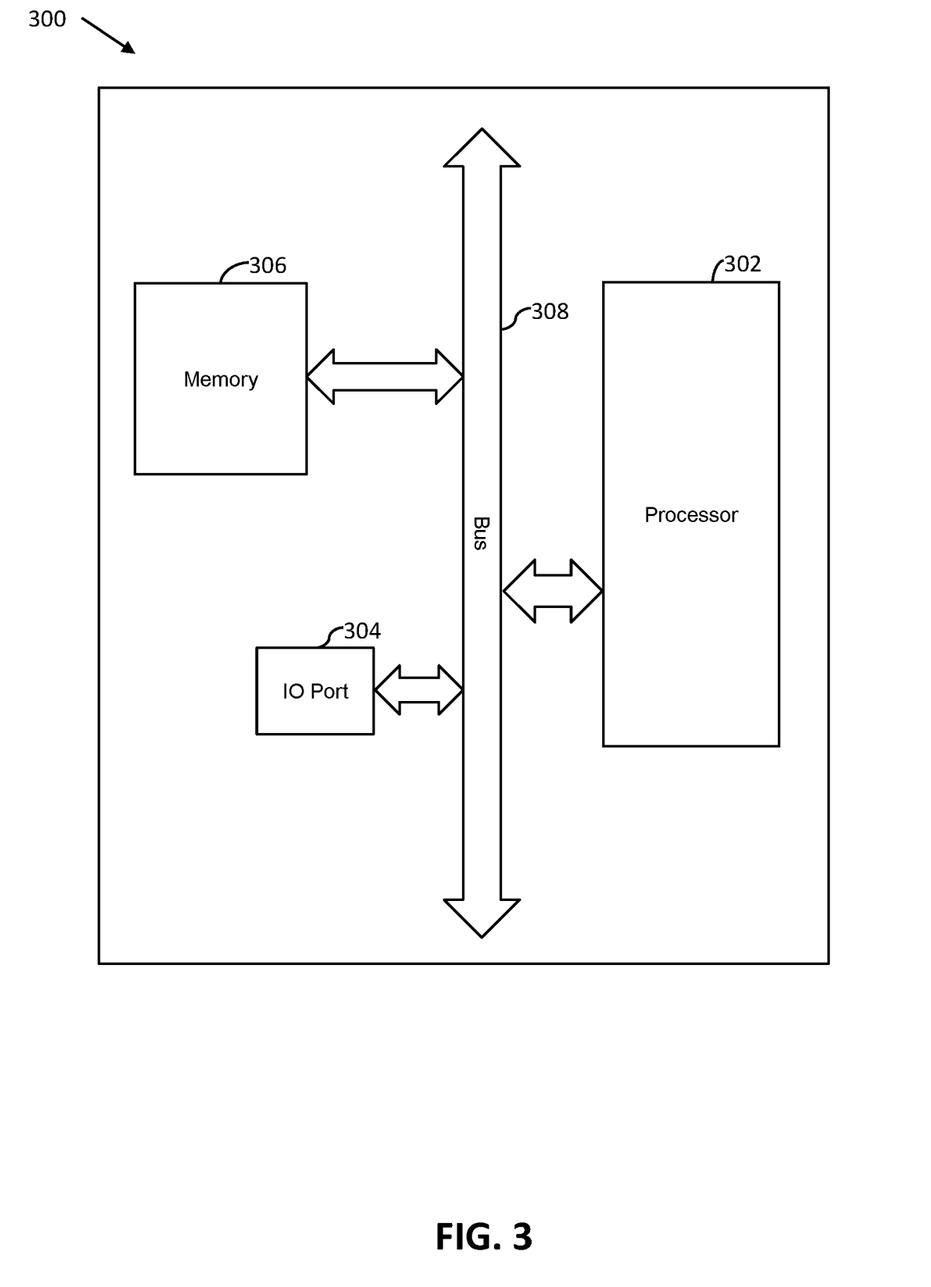
FIG. 3 is a schematic block diagram of a computer system on which various embodiments of the present invention are implemented in accordance with an embodiment of the present invention.

Referring now to FIG. 3, a computer system 300 includes instructions that are required to perform the methodologies described herein. The computer system 300 may be implemented as a server machine or a client machine in a client-server computer network or a peer machine in a peer-to peer or distributed network. The computer system 300 may be realized in the form of a personal computer, a laptop, a server, a set-top box (STB), a tablet, a phablet, a PDA, a cellular telephone, a web appliance, a server, a network router, a network switch, a network bridge, a video game console, or any machine that is capable of executing a set of computer instructions (sequential or otherwise) that are to be executed by the computer system 300. Further, while only a single computer system 300 is illustrated, the term 'computer system' should also be taken to include any system such as the location server 110, the analytics server 112, and the management server 114 that individually or jointly execute a set (or multiple sets) of instructions to perform any one or more of the methodologies discussed herein.

The computer system 300 includes a processor 302, an input/output (IO) port 304, a memory 306 and a system bus 308. The IO port 304 is an interface between the computer system 300 and an external network such as the Internet. The IO port 304 may be connected to input devices such as keyboards, touch-sensitive input devices, microphones, and so on, to accept input from a user. The memory 306 stores sets of instructions to perform the various functions described herein. The IO port 304 and the memory 306 communicate by way of the system bus 308. The processor 302 fetches and executes the sets of instructions from the memory 306.

Certain exemplary methods for monitoring the IV fluid in the IV bag 102 are described with reference to FIGS. 4A and 4B. The order of the steps included in the flowcharts may change in practical implementation. Additionally, certain steps may be deleted, modified, or added to the flowcharts. Moreover, the steps included in the flowcharts may be performed sequentially, or in a distributed manner. Further, the steps may involve additional components or omit certain components in practical implementation.

Figure 4A:
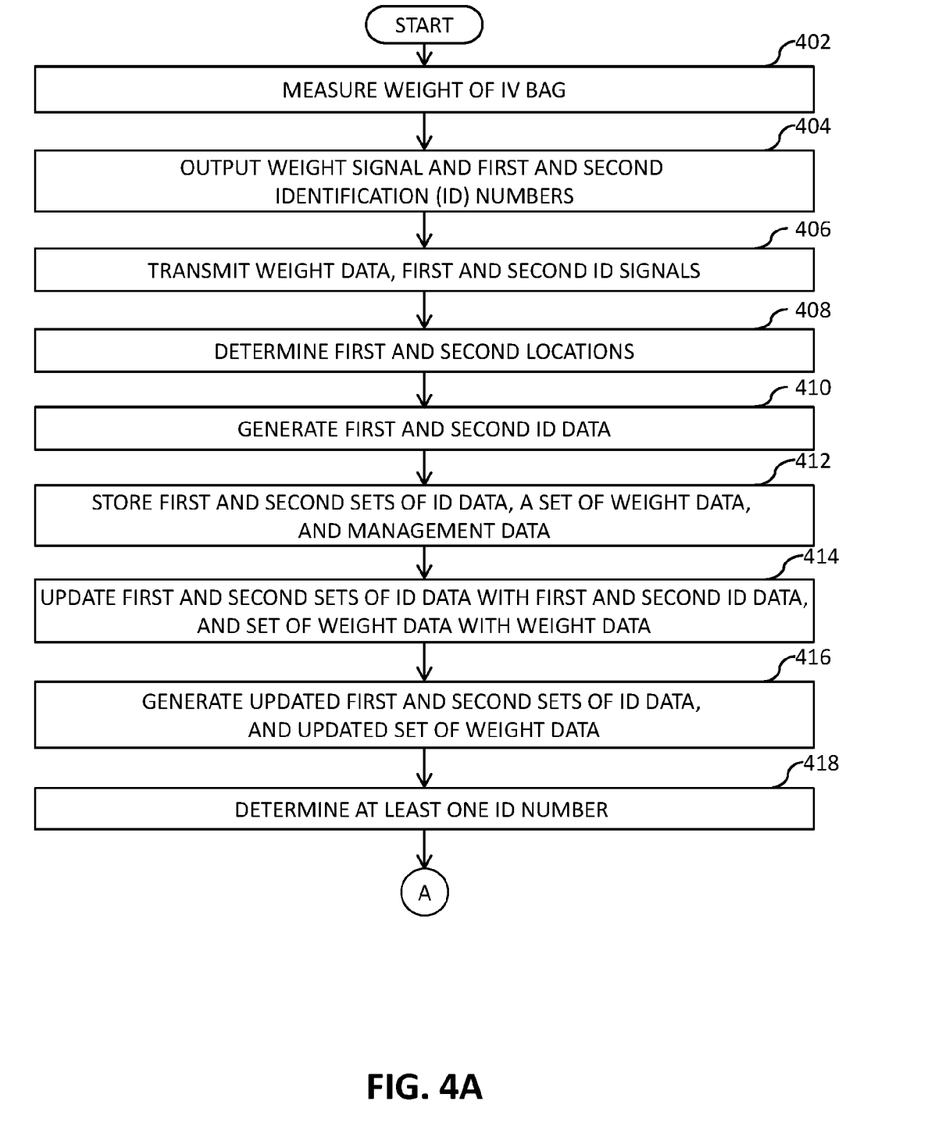
FIGS. 4A and 4B are a flow chart illustrating a method for monitoring IV fluid in an IV bag by the IV fluid monitoring system of FIG. 1 in accordance with an embodiment of the present invention.
Figure 4B:
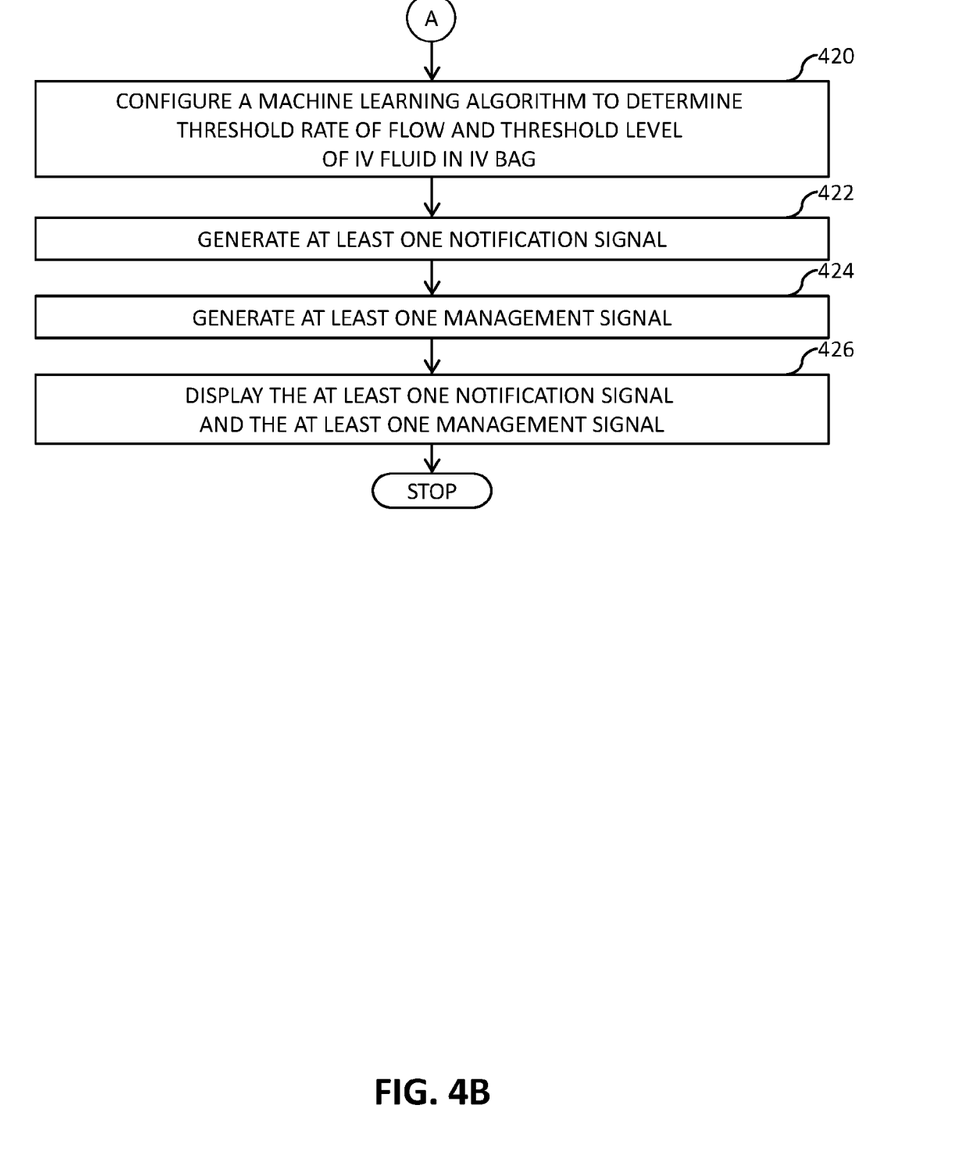

Referring now to FIGS. 4A and 4B, a flow chart illustrating a method for monitoring the IV fluid in the IV bag 102 in accordance with an embodiment of the present invention is shown. At step 402, the weight sensor 202 measures the weight of the IV bag 102. At step 404, the weight sensor 202, the first location tag 204, and the second location tag 210 output the weight signal, ID_NUM1, and ID_NUM2, respectively. At step 406, the first controller 206 transmits the WEIGHT and ID_SIG1, and the second controller 212 transmits the ID_SIG2 to the gateway 108 by way of the first and second transmitters 208 and 214, respectively. At step 408, the gateway 108 determines the first and second locations of the IV bag 102 and the user based on the ID_SIG1 and ID_SIG2, respectively. At step 410, the gateway 108 generates the ID_DAT1 and ID_DAT2. At step 412, the location server 110 stores the first and second sets of ID data, the analytics server 112 stores the set of weight data, and the management server 114 stores the management data. At step 414, the location server 110 updates the first and second sets of ID data with the ID_DAT1 and ID_DAT2, and the analytics server 112 updates the set of weight data with the WEIGHT. At step 416, the location server 110 generates the ID_SET1 and ID_SET2, and the analytics server 112 generates the updated set of weight data. At step 418, the analytics server 112 determines at least one ID number, which corresponds to a user nearest to the IV bag 102. At step 420, the analytics server 112 configures the machine learning algorithm to determine the threshold rate of flow and the threshold weight of the IV fluid in the IV bag 102. The machine learning algorithm operates based on the ID_SET1 and ID_SET2, the updated set of weight data, and a location of user corresponding to the at least one ID number. At step 422, the analytics server 112 generates at least one NOTIFY, which includes the ID_DAT1 of the IV bag 102, the ID number corresponding to the at least one nearest user, and at least one of the threshold rate of flow and the threshold weight of the IV fluid in the IV bag 102. At step 424, the management server 114 generates at least one MANAGE. At step 426, the first user notification device 116 displays the at least one NOTIFY on the first display panel 220, and the second user notification device 118 displays the at least one NOTIFY and the at least one MANAGE on the second display panel 226.

In operation, the weight sensor 202 senses the weight of the IV bag 102 and generates the weight signal. The first location tag 204 stores the ID_NUM1. The first controller 206 receives the weight signal and ID_NUM1 and periodically transmits the WEIGHT and ID_SIG1 by way of the first transmitter 208. The user locator device 120 is associated with the user, who also carries the first user notification device 116, which may be worn by the user as a part of his or her uniform. The second location tag 210 stores the ID_NUM2. The second controller 212 periodically transmits the ID_SIG2 by way of the second transmitter 214. The gateway 108 receives the ID_SIG1, ID_SIG2, and WEIGHT. The gateway 108 determines a location of the IV bag 102 and a location of the user locator device 120 (i.e., a location of the corresponding user carrying the user locator device 120) based on the RSSI of the ID_SIG1 and ID_SIG2. The gateway 108 then transmits the ID_DAT1 and ID_DAT2 to the location server 110. The location server 110 receives and updates the first and second sets of ID data with the ID_DAT1 and ID_DAT2, respectively, to generate the ID_SET1 and ID_SET2, respectively. The location server 110 transmits the ID_SET1 and ID_SET2 to the analytics server 112. The analytics server 112 further receives the WEIGHT and updates the set of weight data to generate the updated set of weight data. The analytics server 112 determines at least one user that is nearest to each of the multiple IV bags. In an embodiment, the analytics server 112 determines that the user, carrying the user device 104, is nearest to the IV bag 102. The analytics server 112 further determines the threshold weight of the IV fluid and the threshold rate of flow of the IV fluid in the IV bag 102 based on the ID_SET1, ID_SET2, the updated set of weight data, and the ID number of the user nearest to the IV bag 102.

In one embodiment, since the weight of the IV fluid in the IV bag 102 is equal to the threshold weight, the analytics server 112 generates the NOTIFY. In another embodiment, since the rate of flow of the IV fluid in the IV bag 102 is equal to the threshold rate of flow, the analytics server 112 generates the NOTIFY. In yet another embodiment, since the weight and the rate of flow of the IV fluid equals the threshold weight and the threshold rate of flow, the analytics server 112 generates the NOTIFY.

In one embodiment, the management server 114 receives the NOTIFY and determines that stock of available IV bags would be administered in one day and hence, should be replenished. The management server 114 generates the MANAGE, which includes a reminder to replenish the stock of IV bags. In another embodiment, the management server 114 receives the NOTIFY, which is generated in a first clock cycle of the first clock signal and includes the ID_NUM2. Further, the management server 114 again receives the NOTIFY, which is generated in a second clock cycle of the first clock signal and includes the ID_NUM2. The second clock cycle is consequent to the first clock cycle of the first clock signal. Hence, the management server 114 determines that the user with the ID_NUM2 failed to respond to the NOTIFY. The management server 114 generates the MANAGE, which includes a report corresponding to the user carrying the user device 104.

The gateway 108 transmits the NOTIFY and MANAGE to the first and second user notification devices 116 and 118. The first user notification device 116 displays the NOTIFY on the first display panel 220 when the ID number form the NOTIFY matches the ID_NUM2. The second user notification device 118 displays the NOTIFY and MANGE on the second display panel 226.

Thus, various embodiments of the present invention offer one or more of the following advantages. The IV fluid monitoring system 100 periodically senses the weight data of each IV bag 102 of the multiple IV bags and location of each user of the set of users. The analytics server 112 uses real-time information as well as stored information of the weight data and the locations of the multiple IV bags and locations of the set of users. Hence, the analytics server 112 accurately estimates a rate of flow of the IV fluid drained out of the IV bag 102, the time required for emptying the IV bag 102, and the time required by the nearest user to reach the corresponding IV bag 102 to determine the threshold weight of the IV fluid in the IV bag 102. Thus, the IV fluid monitoring system 100 avoids interruptions in administration of the IV fluid due to factors such as negligence, lack of skill in identifying the threshold weight, catering to responsibilities other than monitoring the IV fluid, and the like. Further, the IV fluid monitoring system 100 ensures an uninterrupted administration of the IV fluid to a patient irrespective of the location of the user. The analytics server 112 also determines the threshold rate of flow of the IV fluid to detect anomalies in the rate of flow of the IV fluid. Thus, the IV fluid monitoring system 100 detects and avoids irregularities in rate of flow of the IV fluid. The management server 114 generates reminders so that a hospital management committee replenishes the stock of IV bags in order to avoid complete exhaustion of the multiple IV bags. Further, the management server 114 keeps track of the response of the users to the notification signals transmitted to them. Thus, the management server 114 generates a report if a user delays responding to a notification signal. The hospital management committee may take the required action to avoid such delays based on the report. Thus, the IV fluid monitoring system 100 enables the hospital committee to manage the process of administration of the IV fluids to all the patients in the hospital.

While various embodiments of the present invention have been illustrated and described, it will be clear that the present invention is not limited to these embodiments only. Numerous modifications, changes, variations, substitutions, and equivalents will be apparent to those skilled in the art, without departing from the spirit and scope of the present invention, as described in the claims.

The invention claimed is:

1. An intravenous (IV) fluid monitoring system that assists a set of users to monitor and manage a plurality of IV bags, wherein each of the plurality of IV bags includes IV fluid, the IV fluid monitoring system comprising:
   a sensing element, attached to an IV bag of the plurality of IV bags, that determines and outputs weight data and a first identification (ID) signal, wherein the first ID signal includes a first ID number of the IV bag of the plurality of IV bags;
   a user locator device that outputs a second ID signal, wherein the second ID signal includes a second ID number of a user of the set of users;
   a location server that stores first and second sets of ID data, receives first and second ID data, updates the first and second sets of ID data with the first and second ID data, respectively, generates updated first and second sets of ID data, and outputs the updated first and second sets of ID data, wherein the first ID data includes the first ID number and a corresponding first location of the IV bag of the plurality of IV bags, and the second ID data includes the second ID number and a corresponding second location of the user of the set of users, and wherein the first set of ID data includes sets of ID numbers and corresponding locations of the plurality of IV bags, and the second set of ID data includes sets of ID numbers and corresponding locations of the set of users; and
   an analytics server that (i) stores a set of weight data, (ii) receives the weight data and the updated first and second sets of ID data, (iii) updates the set of weight data with the weight data to generate an updated set of weight data, (iv) determines at least one ID number of at least one corresponding user of the set of users based on a proximity of a location of each user of the set of users to the first location of the IV bag of the plurality of IV bags, (v) includes a machine learning algorithm configured to determine a threshold rate of flow of IV fluid of the IV bag of the plurality of IV bags and a threshold weight of the IV fluid in the IV bag of the plurality of IV bags based on at least one of the updated set of weight data, the updated first and second sets of ID data, and a location of the at least one corresponding user of the set of users, and (vi) generates at least one notification signal that includes the first ID data, the at least one ID number of the at least one corresponding user of the set of users, and at least one of the threshold weight and the threshold rate of flow.

2. The IV fluid monitoring system of claim 1, wherein the sensing element includes:
   a weight senor that measures weight of the IV bag of the plurality of IV bags and outputs a weight signal, wherein a voltage level of the weight signal indicates the weight of the IV bag of the plurality of IV, bags;

a location tag that outputs the first ID number; and a controller connected to the weight sensor and the location tag for receiving the weight signal and the first ID number, respectively, and outputting the weight data and the first ID signal.

3. The IV fluid monitoring system of claim 1, wherein the user locator device includes:

a location tag that outputs the second ID number; and a controller connected to the location tag for receiving the second ID number and outputting the second ID signal, wherein the user of the set of users carries the user locator device.

4. The IV fluid monitoring system of claim 1, further comprising a management server that stores management data, receives the at least one notification signal, and generates at least one management signal based on the management data and the at least one notification signal, wherein the at least one management signal includes at least one reminder and at least one report.

5. The IV fluid monitoring system of claim 4, further comprising a user notification device that receives the at least one notification signal, wherein the user notification device includes:

a location tag processor that stores the second ID number, identifies the at least one ID number of the at least one corresponding user of the set of users from the at least one notification signal, compares the second ID number with the at least one ID number of the at least one corresponding user of the set of users from the at least one notification signal, and outputs the at least one notification signal based on the comparison between the second ID number and the at least one ID number of the at least one corresponding user of the set of users from the at least one notification signal; and a display panel that is connected to the location tag processor for receiving and displaying the at least one notification signal, wherein the user of the set of users carries the user notification device.

6. The IV fluid monitoring system of claim 4, further comprising a user notification device that receives the at least one notification signal and the at least one management signal, wherein the user notification device includes:

a display panel for displaying the at least one notification signal and the at least one management signal.

7. The IV fluid monitoring system of claim 1, further comprising a gateway that receives the first and second ID signals, the weight data, the at least one notification signal, and at least one management signal, wherein the gateway determines the first location of the IV bag of the plurality of IV bags and the second location of the user of the set of users, based on the first and second ID signals, respectively, and wherein the gateway transmits the first and second ID data, the weight data, the at least one notification signal, and the at least one management signal.

8. An intravenous (IV) fluid monitoring system that assists a set of users to monitor and manage a plurality of IV bags, wherein each of the plurality of IV bags includes IV fluid, the IV fluid monitoring system comprising:

a sensing element, attached to an IV bag of the plurality of IV bags, that determines and outputs weight data and a first ID signal, wherein the first ID signal includes a first ID number of the IV bag of the plurality of IV bags;

a user locator device that outputs a second ID signal, wherein the second ID signal includes a second ID number of a user of the set of users;

a location server that stores first and second sets of ID data, receives first and second ID data, updates the first and second sets of ID data with the first and second ID data, respectively, generates updated first and second sets of ID data, and outputs the updated first and second sets of ID data, wherein the first ID data includes the first ID number and a corresponding first location of the IV bag of the plurality of IV bags, and the second ID data includes the second ID number and a corresponding second location of the user of the set of users, and wherein the first set of ID data includes sets of ID numbers and corresponding locations of the plurality of IV bags, and the second set of ID data includes a-sets of ID numbers and corresponding locations of the set of users; and an analytics server that (i) stores a set of weight data, (ii) receives the weight data and the updated first and second sets of ID data, (iii) updates the set of weight data with the weight data to generate an updated set of weight data, (iv) determines at least one ID number of at least one corresponding user of the set of users based on a proximity of a location of each user of the set of users to the first location of the IV bag of the plurality of IV bags, (v) determines a threshold rate of flow of IV fluid of the IV bag of the plurality of IV bags and a threshold weight of the IV fluid in the IV bag of the plurality of IV bags based on at least one of the updated set of weight data, the updated first and second sets of ID data, and a location of the at least one corresponding user of the set of users, and (vi) generates at least one notification signal that includes the first ID data, the at least one ID number of the at least one corresponding user of the set of users, and at least one of the threshold weight and the threshold rate of flow.

9. The IV fluid monitoring system of claim 8, wherein the analytics server further includes a machine learning algorithm configured to determine the threshold rate of flow of the IV fluid of the IV bag of the plurality of IV bags and the threshold weight of the IV fluid in the IV bag of the plurality of IV bags based on at least one of the updated set of weight data, the updated first and second sets of ID data, and the location of the at least one corresponding user of the set of users.

10. The IV fluid monitoring system of claim 8, wherein the sensing element includes:

a weight sensor that measures weight of the IV bag of the plurality of IV bags, and outputs a weight signal, wherein a voltage level of the weight signal indicates the weight of the IV bag of the plurality of IV bags;

a location tag that outputs the first ID number; and a controller connected to the weight sensor and the location tag for receiving the weight signal and the first ID number, respectively, and outputting the weight data and the first ID signal.

11. The IV fluid monitoring system of claim 8, wherein the user locator device includes:

a location tag that outputs the second ID number; and a controller connected to the location tag for receiving the second ID number and outputting the second ID signal, wherein the user of the set of users carries the user locator device.

12. The IV fluid monitoring system of claim 8, further comprising a management server that stores management data, receives the at least one notification signal, and generates at least one management signal based on the management data and the at least one notification signal, wherein the at least one management signal includes at least one reminder and at least one report.

13. The IV fluid monitoring system of claim 12, further comprising a user notification device that receives the at least one notification signal and the at least one management signal, wherein the user notification device includes:
   a location tag processor that stores the second ID number, identifies the at least one ID number of the at least one corresponding user of the set of users from the at least one notification signal, compares the second ID number with the at least one ID number of the at least one corresponding user of the set of users from the at least one notification signal, and outputs the at least one notification signal based on the comparison between the second ID number and the at least one ID number of the at least one corresponding user of the set of users from the at least one notification signal; and
   a display panel that is connected to the location tag processor for receiving and displaying the at least one notification signal, wherein the user of the set of users carries the user notification device.

14. The IV fluid monitoring system of claim 12, further comprising a user notification device that receives the at least one notification signal and the at least one management signal, wherein the user notification device includes:
   a display panel for displaying the at least one notification signal and the at least one management signal.

15. The IV fluid monitoring system of claim 8, further comprising a gateway that receives the first and second ID numbers, the weight data, the at least one notification signal, and at least one management signal, wherein the gateway determines the first location of the IV bag of the plurality of IV bags and the second location of the user of the set of users based on the first and second ID signals, respectively, and wherein the gateway transmits the first and second ID data, the weight data, the at least one notification signal, and the at least one management signal.

16. A method for monitoring IV fluid, wherein the method assists a set of users to monitor and manage a plurality of IV bags, wherein each of the plurality of IV bags includes IV fluid, the method comprising:
   outputting weight data and a first ID signal by a sensing element that is attached to an IV bag of the plurality of IV bags, wherein the first ID signal includes a first ID number of the IV bag of the plurality of IV bags;
   outputting a second ID signal by a user locator device, wherein the second ID signal includes a second ID number of a user of the set of users;
   storing first and second sets of ID data in a location server, wherein the first set of ID data includes sets of ID numbers and corresponding locations of the plurality of IV bags, and the second set of ID data includes sets of ID numbers and corresponding locations of the set of users;
   updating the first and second sets of ID data with first and second ID data, respectively, wherein the first ID data includes the first ID number and a corresponding first location of the IV bag of the plurality of IV bags, and the second ID data includes the second ID number and a corresponding second location of the user of the set of users;
   generating updated first and second sets of ID data;
   storing a set of weight data in an analytics server, wherein the set of weight data corresponds to the plurality of IV bags;
   updating the set of weight data with the weight data;
   generating an updated set of weight data;
   determining at least one ID number of at least one corresponding user of the set of users based on a proximity of a location of each user of the set of users to the first location;
   configuring a machine learning algorithm to determine a threshold rate of flow of IV fluid of the IV bag of the plurality of IV bags and a threshold weight of the IV fluid in the IV bag of the plurality of IV bags based on at least one of the updated set of weight data, the updated first and second sets of ID data, and a location of the at least one corresponding user of the set of users; and
   generating at least one notification signal that includes the first ID data, the at least one ID number of the at least one corresponding user of the set of users, and at least one of the threshold weight and the threshold rate of flow.

17. The method of claim 16, wherein determining the weight data and the first ID signal of the IV bag of the plurality of IV bags includes:
   measuring a weight of the IV bag of the plurality of IV bags by a weight sensor;
   outputting a weight signal, wherein a voltage level of the weight signal indicates the weight of the IV bag of the plurality of IV bags;
   outputting the first ID number by a location tag; and
   outputting the weight data and the first ID signal by a controller, wherein the weight data corresponds to the weight signal.

18. The method claim 16, further comprising:
   storing management data by a management server;
   receiving the at least one notification signal by the management server; and
   generating at least one management signal based on the management data and the at least one notification signal, wherein the at least one management signal includes at least one reminder and at least one report.

19. The method of claim 16, further comprising:
   receiving the at least one notification signal and at least one management signal by a user notification device, wherein the user of the set of users carries the user notification device;
   storing the second ID number by a location tag processor of the user notification device;
   identifying the at least one ID number of the at least one corresponding user of the set of users from the at least one notification signal by the location tag processor;
   comparing the second ID number with the at least one ID number of the at least one corresponding user of the set of users from the at least one notification signal by the location tag processor; and
   displaying the at least one notification signal and the at least one management signal on a display panel of the user notification device based on the comparison between the second ID number and the at least one ID number of the at least one corresponding user of the set of users from the at least one notification signal.

20. The method of claim 16, further comprising:
   determining the first location of the IV bag and the second location of the user of the set of users based on the first and second ID signals, respectively; and
   transmitting the first and second ID data.

* * * * *